United States Patent [19]

Stednitz et al.

[11] Patent Number: 5,098,435

[45] Date of Patent: Mar. 24, 1992

[54] CANNULA

[75] Inventors: Denis P. Stednitz, Palm Desert; Michael G. Stednitz, Indio, both of Calif.

[73] Assignee: Alphatec Manufacturing Inc., Palm Desert, Calif.

[21] Appl. No.: 616,632

[22] Filed: Nov. 21, 1990

[51] Int. Cl.$^5$ .................... A61B 17/56; A61B 17/00
[52] U.S. Cl. ........................ 606/73; 606/79
[58] Field of Search .............. 606/59, 61, 62, 63, 606/65, 66, 67, 72, 73, 75, 80, 79, 64; 623/13; 411/387

[56] References Cited

U.S. PATENT DOCUMENTS

| | | | |
|---|---|---|---|
| 126,366 | 4/1872 | Wills | 411/387 |
| 2,242,003 | 5/1941 | Lorenzo | 606/65 |
| 2,278,411 | 4/1942 | Braendel | 606/65 |
| 2,388,482 | 11/1945 | Haynes | 411/387 |
| 2,526,959 | 10/1950 | Lorenzo | 606/66 |
| 2,532,296 | 12/1950 | Giesen | 606/73 |
| 2,570,465 | 10/1951 | Lundholm | 606/65 |
| 3,457,573 | 7/1969 | Patyna et al. | 10/27 FS |
| 3,554,193 | 1/1971 | Konstantinou | 606/65 |
| 4,157,677 | 6/1979 | Deutschenbaur | 411/548 |
| 4,175,555 | 11/1979 | Herbert | 606/73 |
| 4,341,206 | 7/1982 | Perrett et al. | 606/80 |
| 4,383,527 | 5/1983 | Asnis et al. | 606/96 |
| 4,388,921 | 6/1983 | Sutter et al. | 606/71 |
| 4,414,966 | 11/1983 | Stednitz | 606/73 |
| 4,432,358 | 2/1984 | Fixel | 606/66 |
| 4,450,835 | 5/1984 | Asnis et al. | 137/212 |
| 4,463,753 | 8/1984 | Gustilo | 606/73 |
| 4,537,185 | 8/1985 | Stednitz | 606/73 |
| 4,632,100 | 12/1986 | Somers | 606/73 |
| 4,640,271 | 2/1987 | Lower | 606/65 |
| 4,653,489 | 3/1987 | Tronzo | 606/65 |
| 4,743,260 | 5/1988 | Burton | 623/17 |
| 4,827,917 | 5/1989 | Brumfield | 606/64 |
| 4,840,632 | 6/1989 | Kampner | 623/22 |

Primary Examiner—Robert A. Hafer
Assistant Examiner—Michael Brown
Attorney, Agent, or Firm—Knobbe, Martens, Olson & Bear

[57] ABSTRACT

A bone stabilizing system including an improved guide pin consisting of an elongate solid shaft having one or more drilling teeth and self-tapping threads at a first end and a cross-section partially defined by a non-circular circumference. The system also includes a fixation device which comprises a metal cannula defined by a hollow cylindrical shaft having a drilling teeth at one end, an operating tool receiving means at the other end and a plurality of threads therebetween. The drilling teeth each having cutting surfaces positioned obliquely with first and second directions in a diametric plane extending axially through the cannula. The receiving portion is configured to accept an operating tool to rotatingly advance or withdraw the cannula within the fractured bone. The threads are configured with a non-circular circumference while a portion of the threads are tapered. Intersecting a portion of the threads is at least one flute which is defined by two substantially orthogonal surfaces and an elongate slot which penetrates the wall of the cannula so as to provide fluid communication between the flute and the interior hollow portion of the cannula. A transition zone is provided between the drilling portion and the beginning of the threads. The guide pin is provided with a non-circular surface which, together which the interior hollow portion of the cannula, define a pathway through which bone chips may easily pass.

37 Claims, 3 Drawing Sheets

CANNULA

FIELD OF THE INVENTION

This invention relates generally to orthopedic surgical devices and in particular, to fixation screws for stabilizing fractured bones.

BACKGROUND OF THE INVENTION

Over the years various devices and methods have been developed for attending to fractured bones in an effort to achieve an effective healing of the fracture. The problem is ensuring that the splintered bone segments are "fixed" in a sufficiently secure position to prevent slippage or separation of the fractured segments during the healing process. The most common means for securing fractures is an external fixation device which extends into or through the bone fragments substantially orthogonal to the plane of the fracture. The fixation device is preferably directed inwardly into the fractured bone so as to pierce the outer cortex of the fractured bone, cross the medullary canal, and imbed its point in the opposite cortex. While such devices were historically used to temporarily stabilize the bone in preparation for a more permanent device, orthopedic physicians subsequently round these pins to be just as effective for stabilizing the bone during the entire healing process. Since then, these fixation devices have found general acceptance and are now widely used throughout the world.

Early fixation pins were configured with smooth, cylindrical shafts which were passed through pre-drilled holes. As these early pins had no threads about their shafts, the pins did not utilize a threaded engagement of the bone fragments. Rather, the pin was snugly fit within the pre-drilled hole merely to minimize slippage or separation. More contemporary fixation pins have employed a plurality of threads secured about a smooth, cylindrical shaft in order to improve upon the "fixed" nature of the pin within the fractured bone. Many were configured with self-tapping threads, thereby eliminating the need to tap a hole in the bone first. After a hole was drilled, the fixation pins were advanced into the hole, simultaneously tapping the sides thereof.

More modern fixation pins further improve upon the fixation process by eliminating the need to pre-drill a fixation hole in the bone. These pins consist of slenderly configured metal shafts which have a set of drilling teeth at a first end and a recess at the other end for receiving an operating tool. The tool assists in rotating the pin within the bone in order to advance or retract the pin therein. Many fixation pins of this type incorporate a pointed spade configuration at the drilling end wherein one or more obtuse, wedge-shaped, spade surfaces are positioned on opposite sides of a longitudinal axis with knife edges to scrape away the bone when the pin is turned. These fixation pins also employ self-tapping threads positioned along the shaft proximate to the sloping surfaces of the drilling teeth and extend for a distance sufficient to fix the bone on opposite sides of the fracture.

Despite the improvement over earlier devices, there are some disadvantages inherent with some of the self-drilling, self-tapping fixation pins presently available. First of all, it is difficult to construct drilling teeth out of suitably acceptable materials wherein the drilling teeth are sufficiently sharp to maintain the necessary pin advancement rate required by the self-tapping threads. An ineffectively slower advancement rate is achieved with simultaneous drilling of the bone hole in contrast to that achieved if a self-tapping pin were advanced in a pre-drilled hole. As a result, the threads tapped into the bore created by the drilling teeth are partially stripped away due to the slower advancement rate. To avoid this problem, some orthopedic surgeons, in treating a fractured bone, use only a self-tapping fixation screw and therefore pre-drill a bore into the bone. Following the creation of an acceptable bore, the orthopedic surgeon directs the fixation screw through the bone cortex on one side of the marrow, through the marrow, and then into the bore created in the bone cortex on the other side of the marrow.

A second problem develops with such slow advancement rates—that of excessively high temperatures resulting from the frictional engagement of the pin with the bone as the fixation pin is inserted. Often a portion of bone tissue, local to the bore, is exposed to excessive heat. Since bone cells are highly vulnerable to severe heat buildup and have been shown to die at temperatures as low as 105° F., the use of self-drilling fixation pins sometimes results in a small region of dead bone tissue surrounding the pin, sometimes causing the pin to become unsecured. In such events, it is necessary for the stabilization process to be repeated to the discomfort and inconvenience of the patient.

While pre-drilling the fixation holes generally overcomes this problem, it results in a more time consuming surgical procedure. Not only is the additional pre-drilling step involved, but since the orthopedic surgeon is unable to see the interior portions of the pre-drilled hole after the drill bit is removed, the manner in which the fixation screw is advanced occurs solely by feel. The interior surfaces of the bone table, adjacent the marrow, are of a generally porous nature, making it difficult to slide a sharp point over the porous surface. Such circumstances further complicate the use of a self-tapping fixation pin not employing self-drilling means.

Recently there have been developed other variations of fixation pins, such as the cannulated fixation screw disclosed in U.S. Pat. No. 4,537,185 to Stednitz ("the '185 patent"). The fixation device disclosed in the '185 patent is a self-tapping, self-drilling, orthopedic fixation screw for use with a guide pin. The manner in which the cannulated fixation screw is used is significant because of its ability to overcome previous difficulties in accurately directing a fixation screw into a predetermined location. The conventional guide pin, having a relatively long thin shaft with threads and drilling teeth at one end, is first directed into the fractured bone so as to penetrate two or more of the fractured segments while maintaining a certain length of shaft outside the bone. The cannulated fixation screw includes an axial opening extending the entire length therethrough, wherein the opening has a diameter slightly larger than the diameter of the shaft of the guide pin. With such an arrangement, the fixation screw can be placed over the protruding end of the guide pin and rotated, by way of a separate advancing tool, into the bone area surrounding the guide pin. The drilling teeth on the fixation screw provide an opening large enough for the fixation screw to advance when the screw is rotated.

The cannulated fixation screw of the '185 patent further consists of a shaft having a plurality of straight axial flutes defining one side face of several drilling teeth, positioned at the forward end of the screw, and also the cutting face of the self-tapping threads is disposed proximal to the drilling teeth. The flutes consist of two perpendicular surfaces, a first surface being aligned coplanar with a diameter of the shaft. Separating the flutes are a plurality of lands defined by decreasing height threads which assist in exposing the first flute surface in order to provide a self-tapping surface. As with most conventional self-tapping screws, the fixation screw of the '185 patent includes a lead angle of incomplete thread heights, formed adjacent the drilling end of the screw, which provide a gradual increase in the height of the threads carved out in the bone up to the maximum thread height.

The device of the '185 patent is somewhat limited by its positioning of the cutting edge of the flutes in coplanar alignment with the diameter of the shaft. Such a configuration creates a neutral rake angle for tapping the hole through which the screw is directed. Neutral rake angles sometimes result in less accurately developed threads in the side walls of the bone while requiring greater force in advancing the fixation screw.

Another problem with cannulated fixation screws, such as that disclosed in the ,185 patent, is the disposal of bone chips developed adjacent the drilling teeth. While theoretically the chips are removed from the bone by directing the chips outwardly through the flutes and the threads, as a practical matter, not all are removed. Some remain at the end of the bore during advancement of the fixation screw due to clogging of the flutes or threads, thereby impairing the drilling process.

Still another problem exists with the current fixation screws, wherein the self-tapping threads are positioned immediately adjacent the drilling teeth. The absence of a transition zone between the two features increases the likelihood of excessive heat build-up by precluding the ability of the surrounding bone to momentarily cool after being drilled before the self-tapping operation begins. Furthermore, the employment of self-tapping screws about a constant minimum diameter further increases heat build-up by making it more difficult to advance the fixation screw.

It would therefore be a novel improvement to provide a fixation device having self-tapping threads defined by a cutting face with positive rake angles in order to increase its effectiveness. It would be another improvement over the prior art to provide for tapered threads along a portion of the self-tapping threads to assist in the advancement process and contribute to the reduction of heat build-up. In addition, it would be a novel improvement to provide a means for more effectively removing bone chips away from the drilling end of the fixation screw in order to improve the drilling process. Furthermore, it would be a significant improvement over the prior art to provide a fixation screw which employs a transition zone between the drilling teeth and the self-tapping threads in order to further reduce the build-up of heat in the fractured bone. Finally, it would be a significant improvement to provide other means incorporated within the fixation screw to reduce heat buildup and thereby minimize bone cell destruction during the fixation process.

SUMMARY OF THE INVENTION

The present invention provides a system for penetrating fractured bones for the purposes of more effectively stabilizing the fractured segments and enhancing the healing process. The present system includes a fixation device which is configured to more effectively pierce the outer cortex of a fractured bone, cross the medullary canal, and imbed its point in the opposite cortex, in conjunction with an improved guide pin. The present system also includes a guide pin having a partially non-circular configuration which, when used in conjunction with the fixation device, permits the effective passage of bone chips through an interior portion of the fixation device.

The fixation device of the present system comprises a metal cannula defined by a hollow cylindrical shaft having a drilling means at one end, an operating tool receiving means at the other end and a plurality of threads therebetween. One preferred embodiment of the cannula is advantageously constructed of titanium, although other materials are contemplated. Titanium is readily acceptable by body tissue as it is sufficiently porous about its exterior surface to permit bone growth to extend into the surface, thereby providing a more effective stabilization system.

The drilling portion of the cannula comprises one or more drilling teeth, each having cutting surfaces positioned obliquely with first and second directions in a diametric plane extending axially through the cannula. Positioned distally from the drilling portion, the receiving portion consists of a polygonally-sided recess aligned concentrically with the hollow portion of the cannula. The receiving portion is configured so as to accept an operating tool which can be used to rotate the cannula, thereby advancing or withdrawing the cannula within the fractured bone.

Intermediate the drilling portion and the receiving portion is the main body of the shaft characterized first by a featureless length of cylindrical shaft and second by a plurality of self-tapping threads. Intersecting a portion of the threads is at least one flute which is defined by two substantially orthogonal surfaces. The flute is advantageously provided with an elongate slot which penetrates the wall of the cannula so as to provide fluid communication between the flute and the interior hollow portion of the cannula.

In one preferred embodiment, the threads are configured with a non-circular circumference so that a minimum area of contact is maintained between the threads and bone as the cannula is rotated within the bone. By eliminating a circular surface normally associated with prior art devices, the build-up of heat in bone is significantly reduced. In another preferred embodiment, a transition zone is provided between the drilling portion and the beginning of the threads which permits the bone to momentarily cool between the drilling and tapping action. In still another embodiment, a portion of the threads are tapered so as to provide a more gradual development of threads, thereby reducing the force necessary to advance the cannula and further reducing heat build-up.

The flute comprises a cutting surface and a tangential surface positioned substantially orthogonal to the cutting surface, although more acute angles are contemplated. In one preferred embodiment the cutting surface is positioned obliquely with the diametric plane such that a positive rake angle is formed which improves upon the cutting action of the self-tapping threads. The elongate slot is positioned along a portion of the tangential surface. With such an arrangement, the bone chips generated by the rotating self-tapping threads may be passed through the slot and into the interior hollow portion of the cannula.

The present system also includes an improved guide pin consisting of an elongate solid shaft, having one or more drilling teeth and self-tapping threads at a first end, and a cross-section partially defined by a non-circular circumference. The guide pin is provided with a non-circular surface which, together which the interior hollow portion of the cannula, define a pathway through which bone chips may easily pass. Such an arrangement more effectively disposes of the bone chips and reduces the accumulation thereof about the threads of the cannula.

With the present system, the bone stabilizing process is advantageously improved by providing a cannula and guide pin which cooperate to reduce the build-up of heat to the bone and, consequently, the amount of bone cells destroyed, thereby improving upon the "fixed" nature of the system. In addition, the force necessary to advance the cannula is reduced due to the effective disposal of bone chips and the improved configuration of the drilling teeth and the selftapping threads. Finally, the present system is advantageously constructed of titanium or like metal which develops a more secure engagement and acceptance of the cannula in the bone by permitting bone growth directly into the surface of the cannula. Other advantages of the present system may be appreciated by reference to the attached drawings and the detailed description below.

DETAILED DESCRIPTION

Figure 1:
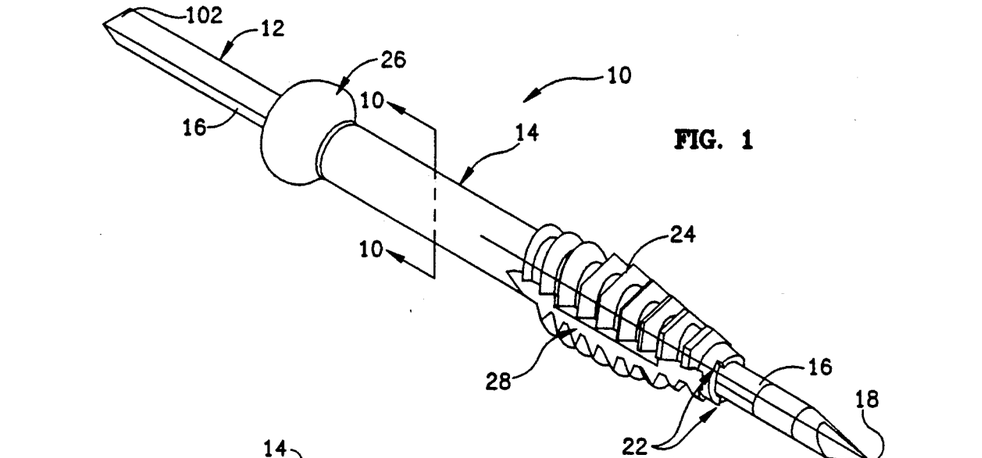
FIG. 1 is a perspective view of one preferred embodiment of the invention showing a first preferred fixation device and a guide pin, wherein the fixation device is a cannula.

Reference is now made to the accompanying drawings wherein like elements are referred to with like numerals. Referring now to FIG. 1, the present invention is a system 10 for stabilizing fractured bones which consists o a guide pin 12 and a cannula 14. Initially it is noteworthy that while the following description is directed to use of the present system 10 in bone reparation procedures, it is contemplated that it may be used in other circumstances requiring the fastening of discreet elements.

The guide pin 12 of the present invention 10 is defined by an elongate shaft 16 provided with a plurality of threads 17 and a drilling means 18 positioned at a forward end thereof for drilling a guide hole into a fractured bone in a predetermined location. The guide pin 12 will be described more fully below in association with FIG. 7.

The cannula 14 is defined by an elongate cylindrical shaft having an axial aperture (not shown) extending therethrough. One preferred embodiment of the cannula 14 is constructed of titanium due to its acceptability to body tissue. With long term uses, a titanium cannula provides for more effective fixation. However, where temporary uses are contemplated, other cannula materials such as stainless steel are employed. In still other embodiments, a titanium nitrate coating is provided about the exterior surface of the cannula to further enhance the durability of the fixation device.

As shown in FIG. 1, the guide pin 12 is configured to slidably receive the cannula 14 about its shaft 16. While the preferred embodiment of the cannula 14 is intended for use with a guide pin 12 for stabilizing fractured bones, similar embodiments of the cannula may be used in other applications requiring improved self-tapping and self-drilling means alone or in conjunction with other components.

Figure 2:
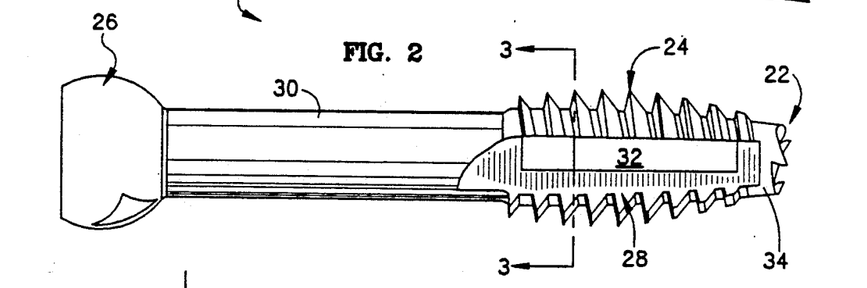
FIG. 2 is a side elevation view of the first preferred cannula of FIG. 1.

As shown in FIG. 2, the cannula 14 comprises a drilling means 22 positioned at a forward end thereof, a self-tapping threading means 24, positioned adjacent the drilling means 22, and a receiving means 26, positioned distally from the drilling means 22, for receiving an operating tool (not shown). The operating tool is used to advance or withdraw the cannula 14 within a fractured bone. Intersecting the self-tapping threading means 24 is preferably a single flute 28 extending from a first point on the cannula, proximate the drilling means 22, to a generally featureless mid-portion 30 of the cannula 14. Disposed within a portion of the flute 28 is an elongate slot 32 penetrating the outer wall of the cannula 14 and providing fluid communication between the exterior of the cannula 14 and the interior of the cannula 14, as discussed further below. Separating the drilling means 22 from the self-tapping threading means 24 is a transition zone 34 defined by a tapered section of the cylindrical shaft.

Figure 3:
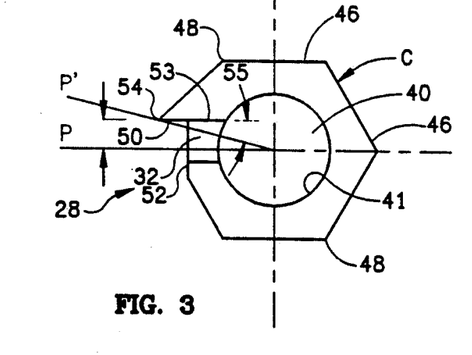
FIG. 3 is a cross-sectional end view of the first preferred cannula taken along line 3—3 of FIG. 2, showing the polygonal circumference and the flute.

Referring now to FIG. 3, a cross-sectional view of the cannula 14, taken about a mid-portion of the self-tapping threading means 24, can be seen. Longitudinally traversing the entire cannula 14 is an axial aperture 40 defined by a cylindrical interior surface 41 of the cannula 14. As indicated above, the axial aperture 40 is in fluid communication with the exterior of the cannula 14 through the elongate slot 32 disposed within the flute 28, as well as through opposite ends of the cannula 14.

In one preferred embodiment, a circumferential surface C of the self-tapping threaded means 24 is defined by a non-circular contour which, in the preferred embodiment, comprises a plurality of contiguous planar surfaces 46 to form a hexagonal contour. By providing a non-circular circumference, the present invention eliminates substantially 360° contact of the cannula 14 to the bone thereby reducing the build-up of heat normally associated with the circular circumferences of the prior art devices. Advantageously, with the present invention, bone contact is maintained only with axial intersections 48 of the contiguous planar surfaces 46. It is contemplated that other embodiments of the cannula 14 will have other polygonally-shaped circumferences, such as pentagons or octagons, etc.

As viewed in FIG. 3, the cross-sectional configuration of the cannula 14 is further defined by the flute 28 which axially intersects the self-tapping threading means 24. In the preferred embodiment, the flute 28 comprises two abutting surfaces, the first surface being a cutting surface 50 and the second surface being a tangential surface 52 positioned substantially orthogonal to the cutting surface 50. The elongate slot 32 is disposed within the tangential surface 52 and is positioned such that a side wall 53 thereof is aligned coplanar with the cutting surface 50. The flute 28 functions to permit the rearward passage of bone chips, generated by the tapping action of the advancing cannula 14, away from the threading means (not shown). As such, the bone chips are directed through the elongate slot 32 and into the axial aperture 40. As the cannula 14 is rotatingly advanced further into the bone, the bone chips directed into the axial aperture are forced out through the receiving means and away from the fractured bone in a manner described more fully below.

The cutting surface 50 of the flute 28 provides a means for tapping threads into the opening created in the bone by the advancing cannula 14. As shown in FIG. 3, one preferred embodiment of the cutting surface 50 is positioned parallel with a first diametric plane P, extending substantially orthogonal to the tangential surface 52. The cutting surface 50 is also positioned oblique to a second diametric plane P' extending through an outer edge 54 of the cutting surface 50. A positive rake angle 55 is thereby defined by the intersection of the cutting surface 50 with the second diametric plane P'. It is worth noting that a positive rake angle advantageously improves the effectiveness of the tapping action by reducing the blunt effects of a cutting surface positioned at a neutral rake angle, i.e., where a cutting surface is aligned with the second diametric plane P'. However, it is contemplated that a neutral rake angle or even a negative rake angle can be used if desired. In one preferred embodiment, the positive rake angle 55 is about 6°-10°, although any positive angle will be effective.

Figure 4:
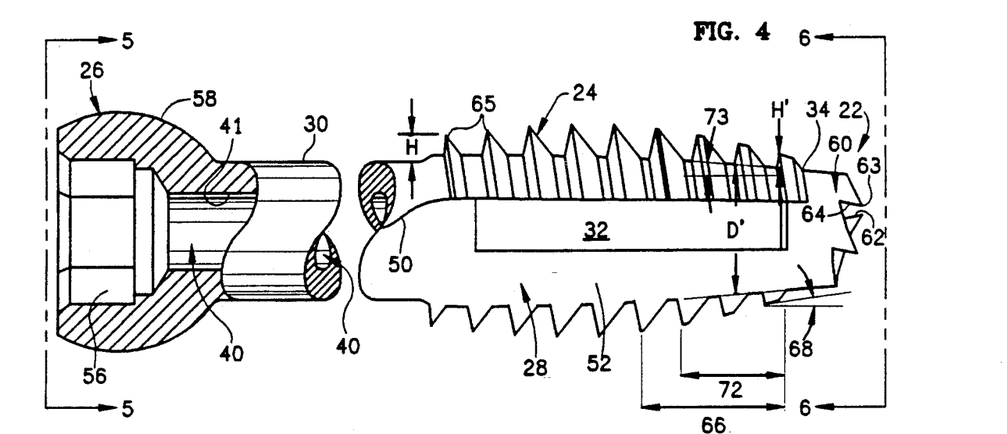
FIG. 4 is an enlarged segmented view of the cannula of FIG. 2 illustrating the two ends of the cannula.

Referring now to FIG. 4, other significant aspects of the present invention may be described. There it may be seen that the receiving means 26, positioned at the rearward end of the cannula 14, comprises a recess 56 disposed within an enlarged collar 58 integral with the mid-portion 30 of the cannula 14. The recess 56 is aligned concentrically with the axial aperture 40 extending therethrough as shown more clearly in FIG. 5. The recess 56 is configured to receive a compatibly-configured operating tool required to advance and withdraw the cannula 14 from a fractured bone. In one preferred embodiment, the recess 56 has a hexagonal perimeter which accepts an operating tool similarly having a hexagonal perimeter.

Referring back to FIG. 4, it can be seen that the drilling means 22 is positioned at the forward end of the cannula 14 and preferably comprises one or more drilling teeth 60 each having a planar cutting face 62 defined by a forward cutting edge 63 and an outer cutting edge 64. In FIG. 4, it is illustrated that the outer cutting edge 64 is positioned oblique to a longitudinal axis extending through the cannula 14. With this oblique arrangement, positive cutting action is achieved, similar to that achieved by the cutting surface 50 of the flute 28, whereby a cutting edge is presented rather than a cutting face. However, where neutral or negative cutting action is desired, the cutting face 62 may be positioned alternatively. When the cannula 14 is rotatingly advanced forward, bone chips are generated by the drilling action. These bone chips are directed into the axial aperture 40 and are directed out of the recess 56. With such an arrangement, the amount of bone chips which accumulate adjacent to the drilling means 22 is significantly reduced, thereby facilitating the drilling process and further reducing the build-up of heat to the bone.

Rearwardly adjacent the drilling means 22 is the transition zone 34 which effectuates a reduction in potential heat buildup by separating the drilling operation from the tapping operation. The transition zone 34 is essentially featureless and is defined by a short tapered section of cylindrical shaft. During surgical advancement of the cannula 14 within a fractured bone, the transition zone 34 provides an opportunity for the adjacent bone to momentarily cool following drilling action and preceding tapping action. It is to be noted that other embodiments having no transition zone 34 are contemplated where it is not necessary to reduce local heat build-up.

Continuing axially along the cannula 14, the self-tapping threading means 24 is shown comprising a plurality of helical threads 65 having thread heights H and a minimum diameter D coincidental with the outer diameter of the featureless mid-portion 30. At a first forward portion of the threading means 24 are a plurality of lead-in threads 66 defined by rearwardly-increasing thread heights H' developed at a lead angle 68. The lead-in threads 66 provide gradual tapping of the bone opening created by the drilling teeth 60 as the cannula 14 is advanced into the bone. In one preferred embodiment, the lead angle 68 is 15°, but other angles are contemplated.

In one preferred embodiment, a second forward portion of the self-tapping threading means 24 is defined by a plurality of tapered threads 72 having a taper angle 73, wherein the tapered threads 72 are defined by a rearwardly-increasing minimum diameter D' extending from the transition zone 34. In one preferred embodiment, the taper angle 73 is 2°, but other angles are contemplated. In the preferred embodiment, one or more of the lead-in threads 66 have tapered characteristics reflective of the tapered threads 72. The remaining threads 65 of the threading means 24 (those not tapered) are characterized by a constant minimum thread diameter D. The incorporation of the transition zone 34 and the tapered threads 72 on one preferred embodiment of the cannula 14 provides for a significant reduction in heat build-up local to the cannula 14.

Intersecting the self-tapping threading means 24 is the flute 28 defined in FIG. 4 by the cutting surface 50 and the tangential surface 52. Traversing a portion of the flute 28 is the elongate slot 32 disposed within the tangential surface 52 and extending inwardly toward the axial opening 40. As indicated above, the bone chips generated by the self-tapping threads 65 are directed rearwardly along the flute 28 and through the elongate slot 32 into the axial aperture 40. The bone chips then exit the recess 56 and away from the cannula 14. With such an arrangement, the amount of bone chips which accumulate between individual threads is significantly reduced, thereby facilitating the tapping process and further reducing the build-up of heat to the bone.

Figure 5:
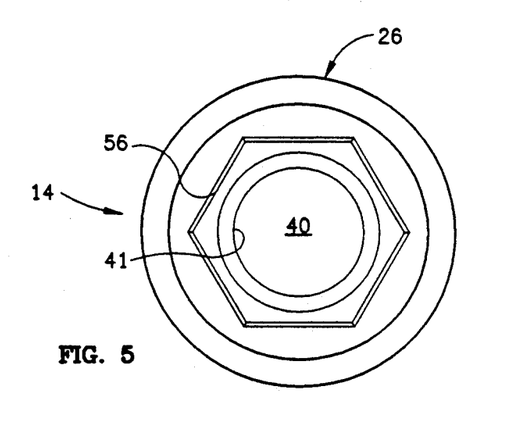
FIG. 5 is a first end view of the cannula taken along line 5—5 of FIG. 4.
Figure 6:
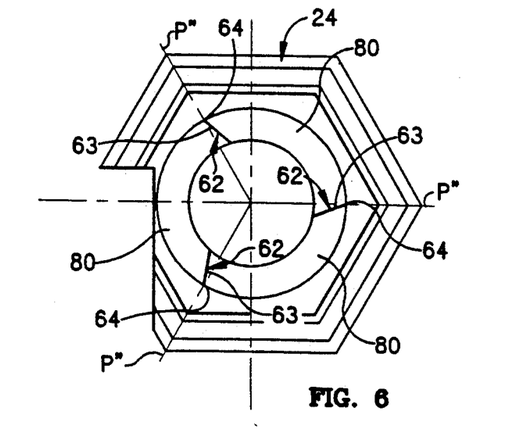
FIG. 6 is a second end view of the cannula taken along line 6—6 of FIG. 4.

Referring now to FIGS. 5 and 6, further details of the drilling teeth 60 may be more fully appreciated. While one or more drilling teeth 60 are contemplated, in the preferred embodiment the cannula 14 is provided with three drilling teeth 60 spaced radially at substantially equal distances apart. As indicated above, the cutting face 62 of each drilling tooth comprises two cutting edges, the forward cutting edge 63 and the outer cutting edge 64, wherein the outer cutting edge 64 is positioned oblique to the longitudinal axis. In FIG. 6, it can be seen that the forward cutting edge 63 is also positioned obliquely with a third diametric plane P" passing through the second cutting edge 64. It is therefore intended that the cutting face 62 be preferably positioned oblique to the third diametric plane P" in two directions, thereby presenting a sharper cutting surface and eliminating the blunt effects of a cutting surface otherwise aligned coplanar with P".

A noteworthy aspect of the present fixation system 10 is that the maximum thread heights of all threads 65, whether tapered or not, are constant about a single revolution. In other words, a single thread has a constant maximum thread height between the cutting surface 50 of the flute 28 and the tangential surface 52 thereof, as shown in FIG. 6. The increase in thread height H' of the lead in threads 66 occurs incrementally wherein an increase takes place in successive threads only at the cutting surface 50 of the flute 28.

Figure 7:
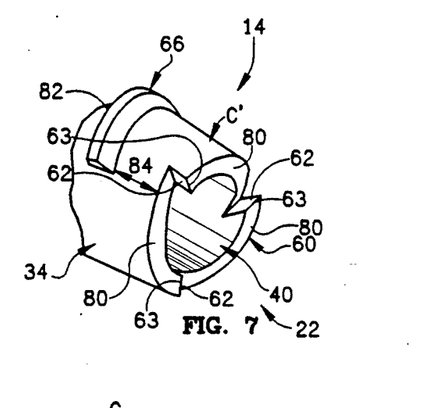
FIG. 7 is an enlarged perspective view of the tip of the first preferred cannula illustrating the drilling teeth and the beginning portions of the self-tapping threads.
Figure 8:
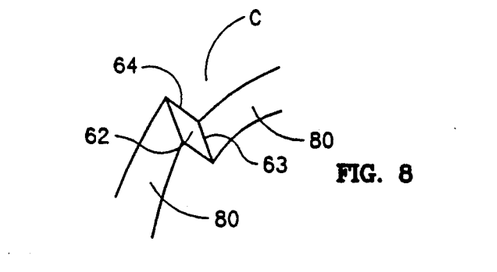
FIG. 8 is an enlarged perspective view of one of the drilling teeth of FIG. 7.

In FIG. 7, it can be seen that the circumference of the drilling means 22 comprises a circumferential surface C'. Each drilling tooth 60 is therefore defined by intersection of the cutting face 62, the circumferential surface C', the interior surface 41 of the axial aperture 40 and an inclined contact surface 80. The intersection of the inclined contact surface 80 with the cutting face 62 defines the forward cutting edge 63 while the intersection of the circumferential surface C' and the cutting face 62 defines the outer cutting edge 64 (shown more clearly in FIG. 8). It is important to note that the drilling teeth 60 are defined by surfaces other than the cutting surface 50 of the flute 28. As such, the drilling teeth are spaced radially about the cannula 14 so as to be out of alignment with the cutting surface 50, thereby reducing local stress to the cannula 14.

Still referring to FIG. 7, the transition zone 34 separates an initial section 82 of lead-in threads 66 at an axial distance 84 from the drilling teeth 60. It is readily apparent that the lead-in threads 66 have incomplete thread heights with frusto-conical contours, thereby providing a gradually increasing height of the tapped threads in the bone.

Figure 9:
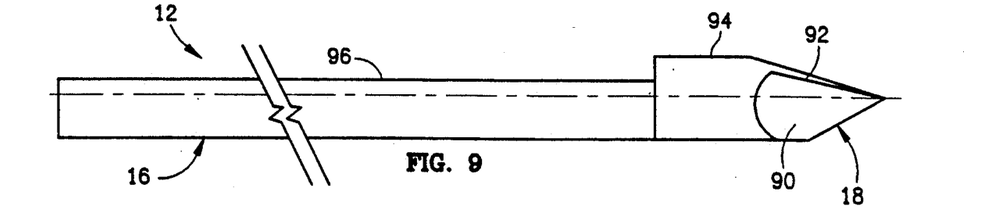
FIG. 9 is a segmented side view of the guide pin.

Referring now to FIG. 9, the details of the guide pin 12 may be more fully appreciated. The guide pin 12 comprises the shaft 16 having the threads 17 and the drilling means 18 positioned at a forward end thereof. The guide pin drilling means 18 comprises preferably one or more drilling teeth 90 each having a cutting edge 92 and having configurations similar to those integral with conventional guide pins in the field of orthopedic medicine.

Figures 10, 11:
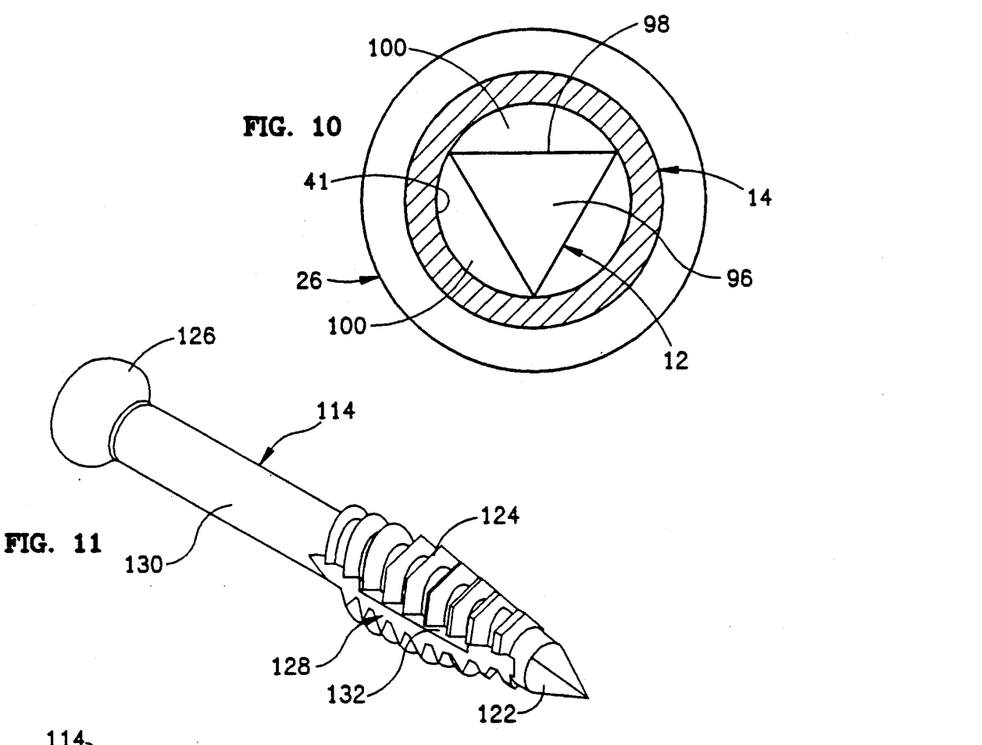
FIG. 10 is a cross-sectional view of the fixation system taken along line 10—10 of FIG. 1, showing the guide pin shaft and the first preferred cannula in cooperation.
FIG. 11 is a perspective view of the second preferred fixation device, wherein the fixation device is a partial cannula.

Adjacent the drilling teeth 90 are the self-tapping threads 17 followed by a forward section 94 of the shaft 16 defined by a cylindrical configuration to support the self-tapping threads 17. Rearwardly adjacent the forward shaft section 94 is a central section 96 of the shaft 16 defined by a non-circular cross-section. As illustrated in FIG. 10, the central section 96 of one preferred embodiment of the guide pin 12 has a triangular cross-section consisting of three intersecting planar surfaces 98. It will be appreciated that an interior passageway 100 is defined by the exterior surface of the guide pin shaft 96 and the interior surface 41 of the axial aperture 40 of the cannula 14. As described above, the bone chips generated during the drilling and tapping operations are directed through the axial aperture 40 along the passageway 100 and outwardly away from the cannula 14. Specifically, the bone chips generated by the drilling action are immediately directed into the axial aperture 40 adjacent the drilling means 22. The bone chips generated by the tapping action are directed into the elongate slot 32 (shown in FIG. 4) of the flute 28 and then further directed into the axial aperture 40. It is to be noted that the guide pin central shaft section 96 may be configured with any non-circular circumference so as to provide a passageway adjacent thereby. For instance the central shaft section 96 may be polygonally shaped or elliptically shaped.

Having described in detail the guide pine 12 and the cannula 14, the manner in which they cooperate in the present system 10 may be discussed. Referring back to FIG. 1, use of the system 10 preferably includes the steps of inserting the guide pin 12 in a designated location within a fractured bone so that an end portion 102 of the shaft 12 protrudes from the bone. The guide pin is preferably directed sufficiently into the bone so that a portion of the shaft 12 extends inwardly beyond the fracture. The cannula 14 is then placed over the end portion 102 of the guide pin and advanced into the bone, using an operating tool which also slips over the end of the guide pin 12 and engages the rearward end of the cannula 14. By rotating the cannula 14 in a preferably clockwise direction, the drilling means 22 of the cannula 14 creates an opening in the bone concentric with the guide pin 12. The cannula 14 is advanced at least until the drilling means 22 engage a portion of the bone entirely inward of the fracture. The cannula 14 is further advanced until the bulbous receiving means 26 tightly engages an exterior surface of the bone, thereby drawing the fractured bone segments together. After the cannula 14 is advanced sufficiently so as to stabilize the fractured bone to assist bone healing, the guide pin 12 is withdrawn leaving the cannula 14 remaining in place. Depending on the needs of the practitioner, the cannula 14 may be maintained permanently or temporarily in place within the bone.

It is also contemplated that the cannula 14 of the present invention may be used without a guide pin 12. In those instances, the cannula 14 is placed at a designated location on the bone and rotatingly advanced using the operating tool so that the drilling means 22 creates a hole in the bone while the threading means taps a plurality of threads in the hole. The bone chips generated by the drilling action are directed into the interior axial opening 40, as described above. It may be necessary, where a guide pin is not used, to provide a starter hole in the bone before inserting the cannula 14 therein. The starter hole will then act as a guide for the accurate advancement of the cannula 14.

Figure 12:
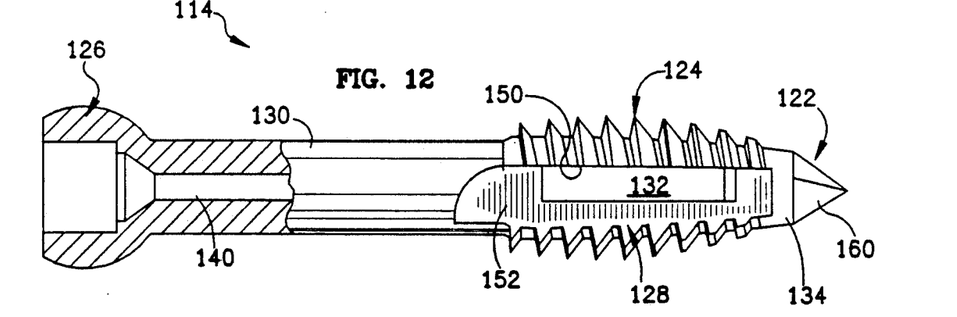
FIG. 12 is a elevational view of the partial cannula of FIG. 11, shown partially in cross-section.
Figure 13:
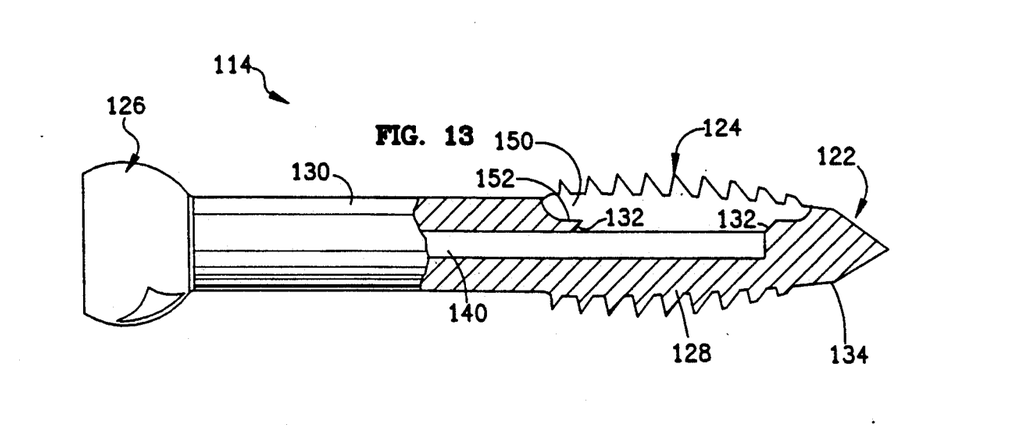
FIG. 13 is an elevational view of the partial cannula of FIG. 11 but illustrated at a 90° orientation therefrom, shown partially in cross-section.

Referring now to FIGS. 11-13, a second preferred embodiment of the present invention may be described. In FIG. 11, it can be seen that the second preferred fixation device is defined by a partial cannula 114 comprising an elongate cylindrical shaft having a drilling means 122 at a first end, self-tapping threading means 124 adjacent the drilling means 122 and a receiving means 126 at a second end thereof. Intersecting the self-tapping threading means 124 is at least one flute 128 extending from a point adjacent the drilling means 122 to a mid-portion 130 of the cannula 114, wherein the flute incorporates an elongate slot 132 therein.

In FIG. 12 it can be seen that the flute 128 comprises two abutting surfaces positioned substantially orthogonally with each other; the first being a cutting surface 150 for the self-tapping threading means 124. The other surface is a tangential surface 152 having the slot 132 disposed therein. The mid-portion 130 of the cannula 114 is defined by an essentially featureless section of cylindrical shaft. Separating the drilling means 122 from the threading means 124 in one preferred embodiment is a transition zone 134 defined similarly by an essentially featureless section of cylindrical shaft.

The drilling means 122 of the second preferred cannula 114 comprises one or more drilling teeth 160 which are configured similarly to the drilling teeth presently found on conventional self-drilling devices commonly available in the art. An example is the drilling teeth of the guide pin described above (see the text in association with FIG. 9). However, it will be appreciated from FIG. 12 that the configurations of the threading means 124, the receiving means 126 and the flute 128 are preferably identical with the analogous components on the first preferred cannula 14 (see FIGS. 2-8).

It is important to note that the flute 128 does not extend forward into the drilling means 122, but terminates proximate to the forward end of the threading means 124. As such, the drilling teeth 160 are not formed by any surface of the flute 128. Furthermore, because the threading means 124 is configured identically with the threading means of the first preferred embodiment, the circumference of the threads in the second preferred embodiment have a non-circular contour and have constant maximum thread heights throughout each 360° revolution of thread.

Referring now to FIG. 13, it may be appreciated that the partial cannula 114 has a different interior configuration than the cannula 14 of the first preferred fixation device. Extending axially through a portion of the partial cannula 114 is an axial aperture 140 which extends from a point adjacent the forward end of the threading means 124 to the receiving means 126. In contrast to the first preferred cannula 14, the axial aperture 140 of the partial cannula 114 does not extend through the drilling means 122. As such, the drilling teeth 160 are configured differently from the first preferred cannula 14 because they are not partially formed by an interior surface of an axial opening (see the above text in association with FIG. 7). In addition, the partial cannula 114 cannot be used with a guide pin, but rather is used independently in orthopedic surgical procedures for the treatment of bone fractures.

When bone chips are generated by radial advancement of the second preferred cannula 114 into a working material, they are disposed of by guiding them along the flute 128, through the slot 132 and into the axial aperture 140 for transmission out of the receiving means. The partial cannula 114 has the advantage of offering a fixation device which is used independent of a guide pin that still provides more effective disposal of bone chips than the present self-drilling screws found in the art. In addition, heat build-up is significantly reduced by providing non-circular circumferences, tapered threads and a transition zone, as more fully described above in association with the first preferred cannula 14. It is also important to note that the present invention should not be limited to bone reparation procedures but may be utilized in other circumstances where it is desired to fasten segmented elements.

The present invention may be embodied in other specific forms without departing from its spirit or essential characteristics. The described embodiment is to be considered, in all respects, only as illustrative and not restrictive, and the scope of the invention is, therefore, indicated by the appended claims rather than by the foregoing description. All changes which come within the meaning and range of equivalency of the claims are to be embraced within their scope.

What is claimed:

1. A bone stabilizing system comprising:
   a cannula having an annular recess at a first end for receiving a device for advancing and retrieving the cannula during bone stabilization, said recess having an interior shoulder surface concentrically aligned with a hollow portion longitudinally traversing said cannula;
   a plurality of self-tapping threads integral with the cannula, said threads having a constant maximum thread height along each 360° revolution of said threads, a first group of said threads characterized by a tapered configuration, a second group of said threads characterized by a lead angle of frustoconical cross-sections, and a third group of said threads characterized by a non-circular circumference, a portion of said plurality of self-tapping threads having characteristics of said first, second and third groups;
   at least one slotted flute traversing a portion of the cannula so as to intersect a plurality of threads, said slotted flute comprising a cutting surface, a tangential surface positioned adjacent to and substantially orthogonally to said cutting surface, and an elongate opening which traverses a portion of said slotted flute and extends inwardly through the cannula into the hollow portion thereof, said cutting surface positioned at an angle from a radial direction of a radial plane taken through the centerline of said cannula;
   at least one drilling tooth positioned at a second end of the cannula, distal from the first end thereof, said drilling tooth having a cutting surface positioned at an angle from the radial direction of the radial plane and at an angle from an axial direction of the radial plane, and
   a transition zone separating the self-tapping threads from the drilling teeth.

2. The system of claim 1 further comprising a guide pin for slidably receiving the hollow portion of the cannula, said guide pin comprising an elongate shaft having a plurality of drilling teeth positioned at a first end of said guide pin and a main shaft portion of said guide pin characterized by a non-circular circumference.

3. The system of claim wherein the cannula is constructed of titanium.

4. A fastening system comprising:
   a cannula defined by an elongate shaft having a hollow portion therein;

means positioned at a first end of said cannula for receiving a tool for advancing and retrieving the cannula during bone stabilization;

drilling means positioned at a second end of the cannula, distal from the first end thereof;

a plurality of threads positioned on the cannula intermediate the receiving means and the drilling means, a first group of said threads being characterized by a non-circular circumference, and at least one slotted flute traversing a portion of the cannula so as to intersect a plurality of threads, said slotted flute comprising a cutting surface, a tangential surface, positioned adjacent to and substantially orthogonally to said cutting surface, and an elongate opening which traverses a portion of said slotted flute and extends inwardly through the cannula into the hollow portion thereof.

5. The system of claim 4 wherein the hollow portion extends partially through the cannula.

6. The system of claim 4 further comprising a guide for slidably receiving the cannula, said guide pin having an elongate shaft.

7. The system of claim 6 wherein the guide pin comprises at least one cutting tooth positioned at a first end of the guide pin and a main shaft portion of the guide pin characterized by a non-circular circumference, wherein said guide pin provides a guide for concentric advancement of the cannula.

8. The system of claim 7 wherein the non-circular circumference of the shaft of the guide pin is characterized by a polygonal contour.

9. The system of claim 4 wherein the maximum height of the threads is constant along each 360° revolution of said threads.

10. The system of claim 4 wherein the cannula further comprises a transition zone separating the threads from the drilling means.

11. The system of claim 4 wherein a second group of the threads is characterized by a tapered configuration and a third group of said threads is characterized by a lead angle defined by frusto-conical cross-sections.

12. A fastening system comprising:

a fixation device defined by an elongate shaft, said fixation device having a drilling means positioned at a first end thereof;

a plurality of threads positioned on the fixation device, and at least one slotted flute traversing a portion of the fixation device so as to intersect the plurality of threads, said slotted flute comprising an elongate opening which traverses a portion of said slotted flute and extends inwardly through the fixation device into a hollow portion thereof.

13. The system of claim 12 wherein the hollow portion extends partially through the fixation device.

14. The system of claim 12 wherein a first group of the threads are characterized by a non-circular circumference.

15. The system of claim 14 wherein a second group of the threads is tapered so as to have a rearwardly-increasing minimum diameter.

16. The system of claim 15 wherein a third group of the threads is characterized by a lead angle defined by frusto-conical cross-sections.

17. The system of claim 12 wherein the fixation device further comprises a transition zone separating the drilling means from the plurality of threads. shaft.

18. The system of claim 17 wherein the transition zone is defined by a segment of featureless cylindrical 19. The system of claim 12 wherein the slotted flute further comprises a cutting surface and a tangential surface positioned adjacent to and substantially orthogonally to said cutting surface.

20. The system of claim 12 further comprising a guide pin having a shaft for slidably receiving the cannula, said shaft partially having a non-circular circumference.

21. A fastening system comprising:

a cannula defined by an elongate shaft having a drilling means positioned at a first end thereof;

a plurality of self-tapping threads integral with the cannula, a first group of threads characterized by a tapered configuration, a second group of threads characterized by a lead angle of frusto-conical cross-sections, a third group of threads characterized by a non-circular circumference, a portion of said self-tapping threads having characteristics of said first, second and third groups, and at least one flute traversing a portion of the cannula so as to intersect a plurality of threads.

22. The system of claim 21 wherein the cannula further comprises a transition zone separating the drilling means and the plurality of self-tapping threads.

23. The system of claim 22 wherein the transition zone is defined by a segment of featureless cylindrical shaft.

24. The system of claim 21 wherein the flute is slotted and comprises an elongate opening which traverses a portion of said flute and extends inwardly through the cannula into a hollow portion thereof.

25. The system of claim 24 wherein the hollow portion extends partially through the cannula.

26. The system of claim 24 wherein the flute further comprises a cutting surface and a tangential surface, positioned adjacent to and substantially orthogonally to said cutting surface, and wherein the elongate opening is disposed with the tangential surface.

27. The system of claim 21 further comprising a guide pin having a shaft for slidably receiving the cannula, said shaft having a non-circular circumference.

28. A fastening system comprising:

a cannula defined by an elongate shaft having a drilling means positioned at a first end thereof;

a plurality of self-tapping threads integral with the cannula, a first group of threads having a non-circular circumference;

a transition zone separating the drilling means and the plurality of self-tapping threads, the transition zone being defined by a short segment of featureless cylindrical shaft, and at least one slotted flute traversing a portion of the cannula so as to intersect a plurality of threads.

29. The system of claim 28 wherein the slotted flute comprises an elongate opening which traverses a portion of said flute and extends inwardly through the cannula into a hollow portion thereof.

30. The system of claim 29 wherein the hollow portion extends partially through the cannula.

31. The system of claim 29 wherein the slotted flute further comprises a cutting surface and a tangential surface, positioned adjacent to and substantially orthogonally to said cutting surface, and wherein the elongate opening is disposed with the tangential surface.

32. The system of claim 28 further comprising a guide pin having a shaft for slidably receiving the cannula, said shaft having a non-circular circumference.

33. A method for fastening segmented elements, said method comprising the steps of:
- inserting a portion of a guide pin into the segment elements, said guide pin having a shaft partially defined by a non-circular circumference;
- sliding a cannula over the guide pin, said cannula defined by an elongate shaft having a hollow portion therein;
- receiving a tool at a first end of said cannula for advancing and retrieving the cannula during element fastening;
- drilling the segmented elements with a second end of the cannula to form an opening in the segmented elements;
- generating a plurality of first element chips proximate to the second end of the cannula;
- directing the first element chips into the hollow portion thereof;
- tapping the opening in the elements with a plurality of self-tapping threads positioned on the cannula;
- generating a plurality of second element chips proximate to the self-tapping threads;
- directing a portion of the second element chips through at least one slotted flute which traverses a portion of the cannula so as to intersect a plurality of threads;
- directing a portion of the second element chips into an elongate slot which traverses a portion of the slotted flute and extends inwardly through a wall of the cannula;
- directing a portion of the first and second element chips into an interior space defined by the non-circular shaft of the guide pin and an interior annular surface of the hollow portion of the cannula so that the first and second element chips exit away from the opening in the bone.

34. The method of claim 33 further comprising the step of removing the guide pin so that the cannula remains fixed to the segmented elements.

35. A method for fastening segmented elements, said method comprising the steps of:
- placing a cannula at a designated location on the segmented elements;
- receiving a tool at a first end of said cannula for advancing and retrieving the cannula during element fastening;
- drilling the segmented elements with a second end of the cannula to form an opening in the elements;
- generating a plurality of element chips proximate to the second end of the cannula;
- tapping the opening in the segmented elements with a plurality of self-tapping threads positioned on the cannula;
- directing a portion of the element chips away from the second end of the cannula through at least one slotted flute which traverses a portion of the cannula so as to intersect a plurality of threads;
- directing a portion of the element chips into an elongate slot which traverses a portion of the slotted flute and extends inwardly through a wall of the cannula;
- directing a portion of the element chips into an interior space defined by an interior annular surface of the cannula so that the element chips exit away from the opening in the element.

36. The method of claim 35 wherein the interior space extends partially through the cannula.

37. The method of claim 35 wherein the step of placing a cannula on the segmented elements is preceded by the step of providing a starter hole in the segmented elements into which the cannula is first placed.

* * * * *